(12) United States Patent
Chaudhari et al.

(10) Patent No.: US 6,608,176 B2
(45) Date of Patent: Aug. 19, 2003

(54) TASTE RECEPTOR FOR UMAMI (MONOSODIUM GLUTAMATE) TASTE

(75) Inventors: Nirupa Chaudhari, Coral Gables, FL (US); Stephen D. Roper, Coral Gables, FL (US)

(73) Assignee: University of Miami, Miami, FL (US)

( * ) Notice: Subject to any disclaimer, the term of this patent is extended or adjusted under 35 U.S.C. 154(b) by 0 days.

(21) Appl. No.: 09/820,809

(22) Filed: Mar. 30, 2001

(65) Prior Publication Data

US 2002/0151052 A1 Oct. 17, 2002

Related U.S. Application Data

(60) Provisional application No. 60/193,454, filed on Mar. 31, 2000.

(51) Int. Cl.[7] .......................... C07K 1/00; C07H 21/04; C12N 1/20; C12P 21/06; G01N 33/566
(52) U.S. Cl. .......................... 530/350; 435/6; 435/7.2; 435/7.21; 435/69.5; 435/252.3; 435/320.1; 435/358; 436/501; 514/2; 536/23.5
(58) Field of Search .................. 530/350; 536/23.5; 435/6, 7.2, 7.21, 69.5, 252.3, 320.1, 358; 436/501; 514/2

(56) References Cited

PUBLICATIONS

Chaudhari, N, Landin, A.M, and Roper, S.D., Nature Neuroscience 3(2)113–119, Feb., 2000.*
Lindemann, B., Nature Neuroscience 3(2)99–100, 2000.*
Chaudhari et al., "The Taste of Monosodium Glutamate: Membrane Receptors in Taste Buds", *Journal of Neuroscience*, Jun. 15, 1996, 16(12):3817–3826.
Chaudhari et al., "Molecular and Physiological Evidence for Glutamate (Umami) Taste Transduction via a G Protein–Coupled Receptor", *Annals New York Academy of Sciences*, pp. 398–406, vol. 855, 1998.
Kurihara et al., "Introductory Remarks on Umami Taste", *Annals New York Academy of Sciences*, pp. 393–397 vol. 855, 1998.
Lin et al., "Physiological Evidence for Ionotropic and Metabotropic Glutamate Receptors in Rat Taste Cells", 1999, *The American Physiological Society*, pp. 2061–2069.
Chaudhari et al., "A Metabotropic Glutamate Receptor Variant Functions as a Taste Receptor", *Nature Neuroscience*, vol. 3, No. 2, Feb. 2000, pp. 113–119.

* cited by examiner

*Primary Examiner*—Yvonne Eyler
*Assistant Examiner*—Michael Brannock
(74) *Attorney, Agent, or Firm*—Venable LLP; Ann S. Hobbs

(57) ABSTRACT

A metabotropic glutamate taste receptor having a molecular weight of approximately 68 kDa, encoded by a cDNA sequence having the mRNA sequence of SEQ ID NO:1 is disclosed, which functions as a umami taste receptor. Also disclosed are cells expressing the cloned receptor and a method of screening for umami mimics using the receptor.

5 Claims, 5 Drawing Sheets

FIG. 1a

SEQUENCE LISTING

<160> NUMBER OF SEQ ID NOS: 14

<210> SEQ ID NO 1
<211> LENGTH: 2838
<212> TYPE: DNA
<213> ORGANISM: Rattus sp.

<400> SEQUENCE: 1

```
gcctggggca ccggcacaca gactagggca gctgggtagc cttacatgtc tgggctgggt      60
tgctgtgtcc ccacaggagg gtgttggagg cagctcgcag ggccaaccag accggccact     120
tcttttggat gggttctgat agctgggcct ccaagagtgc cctgtgctg cgccttgagg      180 aggtggccga gggcgcagtc accattctcc ccaagaggat gtctgttcga gggttcgacc     240
gatacttctc cagccgcacg ctggacaaca acaggcgcaa catctggttt gccgagttct     300
gggaggacaa cttccattgc aagttgagcc gccacgcgct caagaaggga agccacatca     360
agaagtgcac caaccgagag cgcatcgggc aggactcggc ctatgagcag gaggggaagg     420
tgcagttcgt gattgacgct gtgtacgcca tgggccacgc gctgcacgcc atgcaccgtg     480
acctgtgtcc tggccgcgta ggactctgcc ctcgcatgga ccccgtggat ggcacccagc     540
tgcttaagta catcaggaac gtcaacttct caggcattgc ggggaaccct gtaaccttca     600
atgagaacgg agacgcacca gggcgctacg acatctacca gtaccaactg cgcaatggct     660
cggccgagta caaggtcatc ggctcgtgga cagaccacct gcacctcaga atagagcgga     720
tgcagtggcc agggagtggc cagcagctgc cgcgctccat ctgcagtctg ccctgccagc     780
ccggggagcg aaagaagact gtgaagggca tggcttgctg ctggcactgc gagccctgca     840
ccgggtacca gtaccaagtg gaccgctaca cctgtaagac ctgcccctac gacatgcggc     900
ccacagagaa ccgcacgagc tgccagccca tccccatcgt caagttggag tgggactcgc     960
cgtgggccgt gctgcccctc ttcctggccg tggtgggcat cgccgccacg ctgttcgtgg    1020
tggtcacgtt tgtgcgctac aacgataccc ccatcgtcaa ggcctcgggc cgggagctga    1080
gctacgtgct gctggcgggc atctttctgt gctacgccac taccttcctc atgatcgcag    1140
agccggacct ggggacctgt tcgctccgcc gcatcttcct agggctcggc atgagcatca    1200
gctacgcggc cctgctgacc aagaccaacc gcatttaccg catctttgag cagggcaaac    1260
ggtcggtcag tgccccgcgt ttcatcagcc cggcctcgca gctggccatc accttcatcc    1320
tcatctccct gcagctgctc ggcatctgcg tgtggttcgt ggtggacccc tcccactcgg    1380
tggtggactt ccaggaccaa cggacacttg accccgctt tgccagggc gtgctcaagt       1440 gcgacatctc ggacctgtcc ctcatctgcc tgctgggcta cagcatgctg ctgatggtca    1500
cgtgtactgt gtacgccatc aagacccgag gcgtgcccga gaccttcaac gaggccaagc    1560
ccatcggctt caccatgtac accacctgca ttgtctggct ggccttcatc cccatctttt    1620
```

```
ttggcacctc acagtcagcc gacaagctgt acatccagac aaccacactg actgtctccg   1680
tgagtctgag cgcttcagtg tccctgggga tgctctacat gcccaaagtc tacatcatcc   1740
tcttccaccc ggagcagaac gtgccaagc gcaagcgcag tctcaaagcc gtggtcaccg    1800
ccgccaccat gtccaacaag ttcacacaga agggcaactt caggcccaat ggggaagcca   1860
aatcagagct gtgtgagaac ctggagaccc cagcgctggc taccaaacag acctacgtca   1920
cctacaccaa ccatgccatc tagccgggcc gcggagccaa gcaggctaag gagccacaac   1980
ctctgaggat ggcacattgg gccagggccg ttcccgaggg ccctgccgat gtctgcccgc   2040
ctcccgggca tccacgaatg tggcttggtg ctgaggacag tagagacccc ggccatcact   2100
gctgggcaag ccgtggtggg caaccagagg aggccgagtg gctggggcag ttccaggtta   2160
tgccacacac aggtcttcct tctggaccac tgttgggccc agcccaaag cacaggggct    2220 cggtctccag agcccagccc tggcttcctc tccttcctcc tgcctccgtc tgtcctgtgg   2280
gtgaccccgg ttggtccctg ccccgtcttt acgtttctct tccgtctttg ctctgcatgt   2340
gttgtctgtt tgggccctct gcttccatat ttttccattc tgctcctggc cttcccctgc   2400
catctgccct gccccctgcc cctcctccct gagctgcccc atccccgcca tcattttctc   2460
ttctgttccc cctcgatctc atttcctacc agccttcccc ctacttggct tcatccacca   2520
actctttcac cacgttgcaa agagaaaaa aaaggggg ggggaatcac ccctacaaa      2580 aaagcccaaa caaaaactaa tcttgagtgt gtttcgaagt gctgcgtcct cctggtggcc   2640
tgtgtgtccc tgtggcctgc agcctgctcg cccgccctac ccgtctgccg tgtgtcctgc   2700
ccgcccgcct gcccgccttg cccttcctgc taacgacacg gagttcagtg cctgggtgtt   2760
tggtgatggt ctctgatgtg tagcatgtct gtttttatac cgagaacatt tctaataaag   2820
ataaacacat ggttttgc                                                 2838

<210> SEQ ID NO 2
<211> LENGTH: 156
<212> TYPE: DNA
<213> ORGANISM: Rattus sp.

<400> SEQUENCE: 2
gagttcgaca agatcatcaa acgcctactg gaaacatcca atgccagggg tatcatcatc      60
tttgccaacg aggatgacat caggagggtg ttggaggcag ctcgcagggc caaccagacc    120
ggccacttct tttggatggg ttctgatagc tggggc                              156

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 3
cgacaagatc atcaaactgc ctac                                           24

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Primer
```

<400> SEQUENCE: 4
gaagttgacg ttcctgatgt act                                             23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
cagctgggta gccttacatg tct                                             23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 6
tctggagtag gatcaggtgg atg                                             23

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 7
aaaggctgct atctcgtgga ct                                              22

<210> SEQ ID NO 8
<211> LENGTH: 7
<212> TYPE: PRT
<213> ORGANISM: Rattus sp.

<400> SEQUENCE: 8

Met Gly Ser Asp Ser Trp Gly
 1               5

<210> SEQ ID NO 9
<211> LENGTH: 52
<212> TYPE: PRT
<213> ORGANISM: Rattus sp.

<400> SEQUENCE: 9

Glu Phe Asp Lys Ile Ile Lys Arg Leu Leu Glu Thr Ser Asn Ala Arg
 1               5                  10                  15

Gly Ile Ile Ile Phe Ala Asn Glu Asp Asp Ile Arg Arg Val Leu Glu
                20                  25                  30

Ala Ala Arg Arg Ala Asn Gln Thr Gly His Phe Phe Trp Met Gly Ser
            35                  40                  45

Asp Ser Trp Gly
    50

<210> SEQ ID NO 10
<211> LENGTH: 149
<212> TYPE: DNA
<213> ORGANISM: Rattus sp.

<400> SEQUENCE: 10

```
gcctggggca ccggcacaca gactagggca gctgggtagc cttacatgtc tgggctgggt      60
tgctgtgtcc ccacaggagg gtgttggagg cagctcgcag ggccaaccag accggccact     120
tcttttggat gggttctgat agctggggc                                       149
```

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 11

```
taaagaattc tagatggcat ggttggtgta g                                     31
```

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 12

```
atttgaattc agctgggtag ccttacatgt c                                     31
```

<210> SEQ ID NO 13
<211> LENGTH: 604
<212> TYPE: PRT
<213> ORGANISM: Rattus sp.

<400> SEQUENCE: 13

```
Met Gly Ser Asp Ser Trp Gly Ser Lys Ser Ala Pro Val Leu Arg Leu
 1               5                  10                  15

Glu Glu Val Ala Glu Gly Ala Val Thr Ile Leu Pro Lys Arg Met Ser
             20                  25                  30

Val Arg Gly Phe Asp Arg Tyr Phe Ser Ser Arg Thr Leu Asp Asn Asn
         35                  40                  45

Arg Arg Asn Ile Trp Phe Ala Glu Phe Trp Glu Asp Asn Phe His Cys
     50                  55                  60

Lys Leu Ser Arg His Ala Leu Lys Lys Gly Ser His Ile Lys Lys Cys
 65                  70                  75                  80

Thr Asn Arg Glu Arg Ile Gly Gln Asp Ser Ala Tyr Glu Gln Glu Gly
                 85                  90                  95

Lys Val Gln Phe Val Ile Asp Ala Val Tyr Ala Met Gly His Ala Leu
            100                 105                 110

His Ala Met His Arg Asp Leu Cys Pro Gly Arg Val Gly Leu Cys Pro
        115                 120                 125

Arg Met Asp Pro Val Asp Gly Thr Gln Leu Leu Lys Tyr Ile Arg Asn
    130                 135                 140

Val Asn Phe Ser Gly Ile Ala Gly Asn Pro Val Thr Phe Asn Glu Asn
145                 150                 155                 160

Gly Asp Ala Pro Gly Arg Tyr Asp Ile Tyr Gln Tyr Leu Arg Asn
                165                 170                 175

Gly Ser Ala Glu Tyr Lys Val Ile Gly Ser Trp Thr Asp His Leu His
            180                 185                 190

Leu Arg Ile Glu Arg Met Gln Trp Pro Gly Ser Gly Gln Gln Leu Pro
        195                 200                 205

Arg Ser Ile Cys Ser Leu Pro Cys Gln Pro Gly Glu Arg Lys Lys Thr
```

```
              210                 215                 220
Val Lys Gly Met Ala Cys Cys Trp His Cys Glu Pro Cys Thr Gly Tyr
225                 230                 235                 240

Gln Tyr Gln Val Asp Arg Tyr Thr Cys Lys Thr Cys Pro Tyr Asp Met
                245                 250                 255

Arg Pro Thr Glu Asn Arg Thr Ser Cys Gln Pro Ile Pro Ile Val Lys
            260                 265                 270

Leu Glu Trp Asp Ser Pro Trp Ala Val Leu Pro Leu Phe Leu Ala Val
        275                 280                 285

Val Gly Ile Ala Ala Thr Leu Phe Val Val Thr Phe Val Arg Tyr
    290                 295                 300

Asn Asp Thr Pro Ile Val Lys Ala Ser Gly Arg Glu Leu Ser Tyr Val
305                 310                 315                 320

Leu Leu Ala Gly Ile Phe Leu Cys Tyr Ala Thr Thr Phe Leu Met Ile
                325                 330                 335

Ala Glu Pro Asp Leu Gly Thr Cys Ser Leu Arg Arg Ile Phe Leu Gly
                340                 345                 350

Leu Gly Met Ser Ile Ser Tyr Ala Ala Leu Leu Thr Lys Thr Asn Arg
            355                 360                 365

Ile Tyr Arg Ile Phe Glu Gln Gly Lys Arg Ser Val Ser Ala Pro Arg
370                 375                 380

Phe Ile Ser Pro Ala Ser Gln Leu Ala Ile Thr Phe Ile Leu Ile Ser
385                 390                 395                 400

Leu Gln Leu Leu Gly Ile Cys Val Trp Phe Val Val Asp Pro Ser His
                405                 410                 415

Ser Val Val Asp Phe Gln Asp Gln Arg Thr Leu Asp Pro Arg Phe Ala
                420                 425                 430

Arg Gly Val Leu Lys Cys Asp Ile Ser Asp Leu Ser Leu Ile Cys Leu
            435                 440                 445

Leu Gly Tyr Ser Met Leu Leu Met Val Thr Cys Thr Val Tyr Ala Ile
        450                 455                 460

Lys Thr Arg Gly Val Pro Glu Thr Phe Asn Glu Ala Lys Pro Ile Gly
465                 470                 475                 480

Phe Thr Met Tyr Thr Thr Cys Ile Val Trp Leu Ala Phe Ile Pro Ile
                485                 490                 495

Phe Phe Gly Thr Ser Gln Ser Ala Asp Lys Leu Tyr Ile Gln Thr Thr
                500                 505                 510

Thr Leu Thr Val Ser Val Ser Leu Ser Ala Ser Val Ser Leu Gly Met
            515                 520                 525

Leu Tyr Met Pro Lys Val Tyr Ile Ile Leu Phe His Pro Glu Gln Asn
        530                 535                 540

Val Pro Lys Arg Lys Arg Ser Leu Lys Ala Val Val Thr Ala Ala Thr
545                 550                 555                 560

Met Ser Asn Lys Phe Thr Gln Lys Gly Asn Phe Arg Pro Asn Gly Glu
                565                 570                 575

Ala Lys Ser Glu Leu Cys Glu Asn Leu Glu Thr Pro Ala Leu Ala Thr
                580                 585                 590

Lys Gln Thr Tyr Val Thr Tyr Thr Asn His Ala Ile
            595                 600

<210> SEQ ID NO 14
<211> LENGTH: 3884
<212> TYPE: DNA
<213> ORGANISM: Homo sapiens
```

-continued

<400> SEQUENCE: 14

```
ccgagtgaca aggaggtggg agagggtagc agcatgggct acgcggttgg ctgccctcag      60
tccccctgct gctgaagctg ccctgcccat gcccacccag gccgtggggc caggggcctg     120
ccagggctag gagtgggcct gccgttcatg ggtctctagg gatttccgag atgcctggga     180
agagaggctt gggctggtgg tgggcccggc tgccccttttg cctgctcctc agcctttacg     240
gcccctggat gccttcctcc ctgggaaagc ccaaaggcca ccctcacatg aattccatcc     300
gcatagatgg ggacatcaca ctgggaggcc tgttcccggt gcatggccgg ggctcagagg     360
gcaagccctg tggagaactt aagaaggaaa agggcatcca ccggctggag gccatgctgt     420
tcgccctgga tcgcatcaac aacgacccgg acctgctgcc taacatcacg ctgggcgccc     480
gcattctgga cacctgctcc agggacaccc atgccctcga gcagtcgctg acctttgtgc     540
aggcgctcat cgagaaggat ggcacagagg tccgctgtgg cagtggcggc ccacccatca     600
tcaccaagcc tgaacgtgtg gtgggtgtca tcggtgcttc agggagctcg gtctccatca     660
tggtggccaa catccttcgc ctcttcaaga taccccagat cagctacgcc tccacagcgc     720
cagacctgag tgacaacagc cgctacgact tcttctcccg cgtggtgccc tcggacacgt     780
accaggccca ggccatggtg gacatcgtcc gtgccctcaa gtggaactat gtgtccacag     840
tggcctcgga gggcagctat ggtgagagcg gtgtggaggc cttcatccag aagtcccgtg     900
aggacggggg cgtgtgcatc gcccagtcgg tgaagatacc acgggagccc aaggcaggcg     960
agttcgacaa gatcatccgc cgcctcctgg agacttcgaa cgccagggca gtcatcatct    1020
ttgccaacga ggatgacatc aggcgtgtgc tggaggcagc acgaagggcc aaccagacag    1080
gccatttctt ctggatgggc tctgacagct ggggctccaa gattgcacct gtgctgcacc    1140
tggaggaggt ggctgagggt gctgtcacga tcctccccaa gaggatgtcc gtacgaggct    1200
tcgaccgcta cttctccagc cgcacgctgg acaacaaccg gcgcaacatc tggtttgccg    1260
agttctggga ggacaacttc cactgcaagc tgagccgcca cgccctcaag aagggcagcc    1320
acgtcaagaa gtgcaccaac cgtgagcgaa ttgggcagga ttcagcttat gagcaggagg    1380
ggaaggtgca gtttgtgatc gatgccgtgt acgccatggg ccacgcgctg cacgccatgc    1440
accgtgacct gtgtcccggc cgcgtggggc tctgcccgcg catggaccct gtagatggca    1500
cccagctgct taagtacatc cgaaacgtca acttctcagg catcgcaggg aaccctgtga    1560
ccttcaatga gaatggagat gcgcctgggc gctatgacat ctaccaatac cagctgcgca    1620
acgattctgc cgagtacaag gtcattggct cctggactga ccacctgcac cttagaatag    1680
agcggatgca ctggccgggg agcgggcagc agctgccccg ctccatctgc agcctgccct    1740
gccaaccggg tgagcggaag aagacagtga agggcatgcc ttgctgctgg cactgcgagc    1800
cttgcacagg gtaccagtac caggtggacc gctacacctg taagacgtgt ccctatgaca    1860
tgcggcccac agagaaccgc acgggctgcc ggcccatccc catcatcaag cttgagtggg    1920
gctcgccctg gcgtgctg cccctcttcc tggccgtggt gggcatcgct gccacgttgt    1980
tcgtggtgat cacctttgtg cgctacaacg acacgcccat cgtcaaggcc tcgggccgtg    2040
aactgagcta cgtgctgctg gcaggcatct tcctgtgcta tgccaccacc ttcctcatga    2100
tcgctgagcc cgaccttggc acctgctcgc tgcgccgaat cttcctggga ctagggatga    2160
gcatcagcta tgcagccctg ctcaccaaga ccaaccgcat ctaccgcatc ttcgagcagg    2220
gcaagcgctc ggtcagtgcc ccacgcttca tcagccccgc ctcacagctg gccatcacct    2280
```

```
tcagcctcat ctcgctgcag ctgctgggca tctgtgtgtg gtttgtggtg gaccctccc    2340
actcggtggt ggacttccag gaccagcgga cactcgaccc ccgcttcgcc agggtgtgc    2400
tcaagtgtga catctcggac ctgtcgctca tctgcctgct gggctacagc atgctgctca   2460
tggtcacgtg caccgtgtat gccatcaaga cacgcggcgt gcccgagacc ttcaatgagg   2520
ccaagcccat tggcttcacc atgtacacca cttgcatcgt ctggctggcc ttcatcccca   2580
tcttctttgg cacctcgcag tcggccgaca agctgtacat ccagacgacg acgctgacgg   2640
tctcggtgag tctgagcgcc tcggtgtccc tgggaatgct ctacatgccc aaagtctaca   2700
tcatcctctt ccacccggag cagaacgtgc ccaagcgcaa gcgcagcctc aaagccgtcg   2760
ttacggcggc caccatgtcc aacaagttca cgcagaaggg caacttccgg cccaacggag   2820
aggccaagtc tgagctctgc gagaaccttg aggcccagc gctggccacc aaacagactt    2880
acgtcactta caccaaccat gcaatctagc gagtccatgg agctgagcag caggaggagg   2940
agccgtgacc ctgtggaagg tgcgtcgggc cagggccaca cccaagggcc cagctgtctt   3000
gcctgcccgt gggcacccac ggacgtggct tggtgctgag gatagcagag cccccagcca   3060
tcactgctgg cagcctgggc aaaccgggtg agcaacagga ggacgagggg ccgggcggt    3120
gccaggctac cacaagaacc tgcgtcttgg accattgccc ctcccggccc caaaccacag   3180
gggctcaggt cgtgtgggcc ccagtgctag atctctcct cccttcgtct ctgtctgtgc    3240
tgttggcgac ccctctgtct gtctccagcc ctgtctttct gttctcttat ctctttgttt   3300
caccttttcc ctctctggcg tccccggctg cttgtactct tggccttttc tgtgtctcct   3360
ttctggctct tgcctccgcc tctctctctc atcctctttg tcctcagctc ctcctgcttt   3420
cttgggtccc accagtgtca cttttctgcc gttttctttc ctgttctcct ctgcttcatt   3480
ctcgtccagc cattgctccc ctctccctgc caccttccc cagttcacca aaccttacat    3540
gttgcaaaag agaaaaaagg aaaaaaatc aaaacacaaa aaagccaaaa cgaaaacaaa    3600
tctcgagtgt gttgccaagt gctgcgtcct cctggtggcc tctgtgtgtg tccctgtggc   3660
ccgcagcctg cccgcctgcc ccgcccatct gccgtgtgtc ttgcccgcct gcccgcccg    3720
tctgccgtct gtcttgcccg cctgcccgcc tgcccctcct gccgaccaca cggagttcag   3780
tgcctgggtg tttggtgatg gttattgacg acaatgtgta gcgcatgatt gtttttatac   3840
caagaacatt tctaataaaa ataaacacat ggttttgcaa aaaa                    3884
```

TASTE RECEPTOR FOR UMAMI (MONOSODIUM GLUTAMATE) TASTE

This application claims the benefit of priority application U.S. Ser. No. 60/193,454 filed Mar. 31, 2000, the entire contents of which are hereby incorporated herein by reference.

This work was supported, at least in part, by funding received from NIH/NIDCD (DC 03013). The United States government may have rights to the invention disclosed herein, accordingly.

BACKGROUND OF THE INVENTION

1. Field of the Invention

The invention relates to the identification and isolation of a G protein-coupled receptor cloned from rat taste buds and functionally expressed in Chinese hamster ovary (CHO) cells. The receptor couples negatively to a cAMP cascade, and has been identified as a taste receptor for glutamate.

2. Description of Related Art

Chemoreceptor cells in taste buds monitor the chemical environment of the oral cavity and generate signals that lead to taste perceptions. Taste transduction for simple salts involves altered permeation of the cell membranes of receptors by ions such as $Na^+$, $K^+$ or $H^+$.[1] The resulting receptor currents in taste bud cells stimulate neurotransmitter release to excite sensory afferents, ultimately leading to perceptions such as 'salty' or 'sour'. Taste transduction for larger organic molecules, such as sugars, amino acids or a heterogeneous collection of compounds that elicit perception of bitterness, is thought to include binding at specific receptors on the taste cell plasma membrane.[1,2]

Some of the proteins that orchestrate this plethora of sensory transduction mechanisms have been identified using molecular biological methods. Taste receptor cells express G proteins, including α-gustducin[3], a-transducin[4], a number of additional Gα subunits[5,6], several Gβ subunits and a taste-specific Gγ[7]. Phosphodiesterases[8] and a cyclic nucleotide-gated channel[8] cloned from mammalian taste buds could potentially participate in sensory transduction pathways. Epithelial sodium channels demonstrated in taste buds presumably underlie 'salty' and 'sour' transduction[9–11]. Detectable receptor activity for 'bitter' stimuli is found in membrane preparations from taste tissue[12]. Although a number of candidate taste-G protein-coupled receptors (GPCRs) have been proposed[13–15], their functional significance in taste transduction has not been established[2].

Sweet, sour, salty, bitter, discussed hereinabove, and umami constitute basic taste qualities. Umami denotes the taste of the glutamate moiety in monosodium L-glutamate (L-MSG), a compound that occurs naturally in protein-rich and other foods. Taste transduction for glutamate is hypothesized to entail stimulation of neurotransmitter-like ionotropic and metabotropic glutamate receptors[16–18]. A number of ionotropic glutamate receptors are expressed in lingual tissue, although none seems preferentially localized to taste buds[17]. Metabotropic glutamate receptors (mGluR1-8) constitute a family of GPCRs that are found in many neuronal cells[19]. In taste receptor cells, molecular, physiological and behavioral evidence implicates a metabotropic receptor similar or identical to mGluR4 in taste transduction for L-glutamate[20]. Such evidence includes the findings that mGluR4 is expressed in rat taste buds[17,21] and that an mGluR4-selective ligand, L-AP4, mimics the taste of L-MSG in conditioned taste aversion in rats[17] and in human psychophysical measurements[22]. Further, both L-MSG and L-AP4 interact synergistically with nucleotide monophosphates to elicit umami taste responses[23,24]. Additionally, stimulating taste buds with glutamate decreases cellular cAMP[46] and alters membrane conductances[25], a signaling cascade also triggered by mGluR4. Collectively, these findings are consistent with the transduction of L-glutamate taste by an mGluR4-like receptor. Nevertheless, several lines of evidence indicate apparent discrepancies between umami taste and the properties of mGluR4. The concentrations of glutamate needed to elicit taste and to activate the neurotransmitter receptor mGluR4 differ markedly. The detection threshold for L-MSG in recordings from sensory afferents is 0.1–0.3 mM in juvenile and 1–3 mM in adult rodents[26,27], whereas mGluR4 requires glutamate in the micromolar range. Further, the ability of glutamate agonists to stimulate mGluR4 does not correlate fully with their umami taste[28]. Additionally, umami taste does not seem to be blocked by a known antagonist of mGluR4[23]. These observations suggest that the receptors transducing umami taste may differ significantly from mGluR4, particularly in the glutamate-binding domain.

The glutamate-binding domain of the mGluR is contained within the large extracellular N terminus. Although detailed structural information is lacking, a model of the N terminus of mGluRs is based on the structure of a bacterial periplasmic leucine-isoleucine-valine binding protein (LIVBP)[29]. Experimental verification of this model includes mutation of contacting amino acids[29], expression of truncated extracellular domains that retain binding characteristics[30] and chimeric receptors with distinct agonist sensitivities[31]. Thus, the extracellular N terminus might be a plausible site for differences between neurotransmitter and taste receptors for glutamate.

Thus, while sensory transduction for many taste stimuli such as sugars, some bitter compounds and amino acids is thought to be mediated via G protein-coupled receptors (GPCRs), no such receptors that respond to taste stimuli have heretofore been identified. Monosodium L-glutamate (L-MSG), a natural component of many foods, is an important gustatory stimulus believed to signal dietary protein. L-MSG, which conveys the umami taste, is often employed by industry to overcome or mask the bitterness associated with protein hydrolyzates used in food and health care products. Therefore, a need exists to identify taste receptors responsible for umami taste sensations in order to better understand the physiological and biochemical mechanisms behind such taste sensations. Identification of the umami taste receptor and its functional properties would permit, inter alia, food scientists tailor ligands to enhance or mimic the umami taste perception via this receptor.

SUMMARY OF THE INVENTION

The invention relates to the identification and isolation of a GPCR cloned from mammalian taste buds and functionally expressed in CHO cells. The receptor couples negatively to a cAMP cascade and shows an unusual concentration-response relationship. The similarity of its properties to MSG taste suggests that this receptor is a glutamate receptor responsible for the umami taste sensation.

A preferred embodiment of the invention is a rat metabotropic glutamate taste receptor having a molecular weight of approximately 68 kDa, encoded by the amino acid sequence of SEQ ID NO:13. The receptor functions as a umami taste receptor. The receptor exhibits a truncated extracellular N-terminal domain comprising about 50% fewer amino acids than are present in neurotransmitter mGluR4 metabotropic glutamate receptors.

Another preferred embodiment is an isolated mRNA molecule encoding a rat metabotropic glutamate taste receptor, the mRNA having the nucleic acid sequence of SEQ ID NO:1.

Another preferred embodiment is an isolated mRNA molecule encoding a metabotropic glutamate taste receptor comprising a subsequence of nucleic acid sequence of SEQ ID No.:14 having at least 85% sequence identity to SEQ ID NO.:1.

Yet another embodiment is a mammalian cell transfected with cDNA encoding a rat metabotropic glutamate taste receptor of SEQ ID NO.: 13, wherein the cDNA expressed in the mammalian cell is capable of being translated into immunologically recognizable metabotropic glutamate taste receptors. Preferably, the mammalian cell is a Chinese hamster ovary cell. The expressed metabotropic glutamate taste receptors in the Chinese hamster ovary cell exhibit an $EC_{50}$ of about 250 to about 300 µM glutamate.

Still another preferred embodiment of the invention is a method of screening samples for umami mimicking compounds comprising transfecting mammalian cells with cDNA encoding metabotropic glutamate taste receptor mRNA, the mRNA comprising the nucleic acid sequence of SEQ ID NO:1. The transfected cells are cultured in an environment that promotes expression of immunologically recognizable metabotropic glutamate taste receptors, and are then treated with a compound that induces cAMP production. The cells are incubated with a sample containing a potential umami mimicking compound capable of binding to the metabotropic glutamate taste receptors. Introduction of the sample containing the potential umami mimicking compound occurs simultaneously with introduction of the compound that induces cAMP. After exposure to such a sample, the amount of cAMP produced is measured. Thereafter, suppression of cAMP production is correlated with umami mimicking compound binding to the metabotropic glutamate taste receptors. Preferably, the transfected cells are Chinese hamster ovary cells. Preferably, the compound that induces cAMP production comprises forskolin.

BRIEF DESCRIPTION OF THE DRAWINGS

The invention is further explained by the following Figures in which:

FIG. 1a depicts the 5' end of the mGluR4 cDNA from taste papillae (SEQ ID NO.:10, lower lines) is aligned with the corresponding region of mGluR4 cDNA from brain (SEQ ID NO.:2, upper lines), together with respective amino acid sequences for the taste (SEQ ID NO.:8) and brain (SEQ ID NO.: 9) receptors, respectively;

DETAILED DESCRIPTION OF THE PREFERRED EMBODIMENTS

Figure 1B:
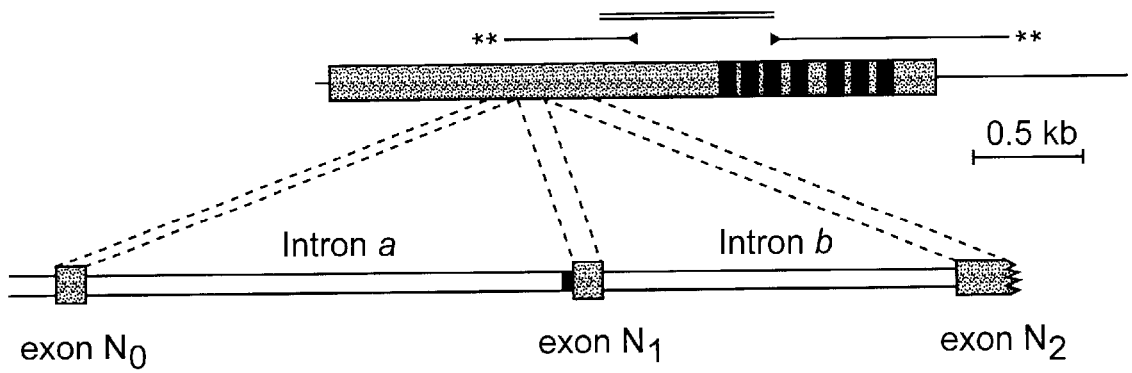
FIG. 1b depicts a schematic showing the full-length cDNA for mGluR4 from brain, including 5' and 3' untranslated regions (line), translated region (shaded bar), and putative regions encoding seven putative transmembrane segments (gray stripes)
Figure 1C:
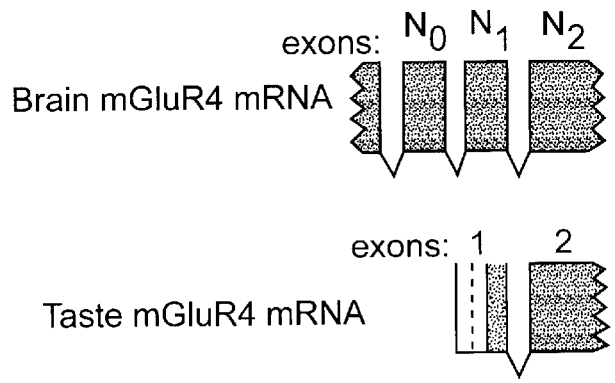
FIG. 1c shows a cartoon depiction of mGluR4 mRNA from brain having several exons upstream of $N_0$, whereas mGluR4 mRNA derived from taste tissue begins with an extended exon $N_1$ spliced to exon $N_2$.
Figure 1D:
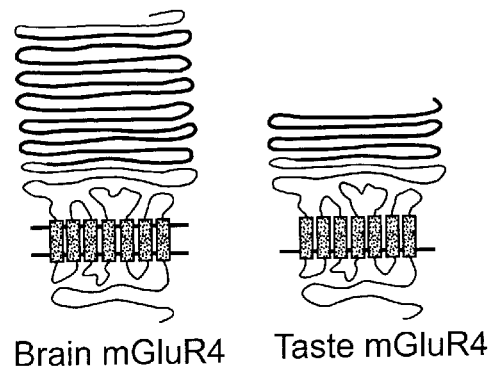
FIG. 1d shows the predicted transmembrane topology of brain-mGluR4 and taste-mGluR4 showing the truncated extracellular N terminal domain followed by seven putative transmembrane helices and cytoplasmic C terminus, wherein the LIVBP-like glutamate-binding domain and its truncated version are shown in heavy lines.

An unusual variant of mGluR4 was found to be expressed in rat lingual epithelium. This variant, labeled taste mGluR4, was predicted to lack approximately half the N terminus of mGluR4, including a large portion of the LIVBP-like putative glutamate-binding domain. Upon sequencing, this rat taste receptor was indeed determined to be a variant of brain-derived neurotransmitter mGluR4.

Rat taste mGluR4 cDNA expressed in CHO cells conferred to these cells sensitivity to L-glutamate at concentrations about 100-fold higher than needed for brain-derived neurotransmitter mGluR4. The expression level of taste mGluR4 was negatively coupled to cAMP concentration. These findings correspond well with the concentrations of glutamate needed to elicit umami taste and resolve the discrepancy between neurotransmitter receptors for glutamate and taste receptors for glutamate. Such differences are likely due, at least in part, to structural differences between the N termini of the taste and neurotransmitter mGluR4 proteins.

Rat neurotransmitter metabotropic glutamate receptor mRNA exhibits substantial identity to human neurotransmitter metabotropic glutamate receptor mRNA sequences (BLAST 2 Sequence Results, version BLASTN 2.1.2, showing 88% identity, gaps=8/2962 (0%), score=3753 bits (1952)). Thus, the rat taste mGluR4 of SEQ ID NO.:1 should display similarly high level of identity with the corresponding human taste receptor, which is expected to be a subsequence of SEQ ID NO.14. In particular, at least 85% sequence identity is expected between SEQ ID NO.:1 and the portion of SEQ ID NO.:14 corresponding to the human taste metabotropic glutamate receptor. Preferably, 90%, and more preferably 95% identity would exist. The sequence of human neurotransmitter metabotropic glutamate receptor type 4 is disclosed by Flor et al., in *Neuropharmacology* 34 (2), 149–155 (1995), the disclosure of which is hereby incorporated herein by reference.

One may also anticipate essentially identical amino acid sequences having minor modifications arising from, for example, nucleic acid having one or more point mutations, that provide for proteins that are functionally identical to the human and rat umami taste receptor proteins disclosed herein. Such protein analogues having minor modifications that do not impair the taste receptor behavior of these proteins are embraced by the invention.

The invention is further illustrated in the following non-limiting examples.

EXAMPLES

Methods
Tissues and RNA

All tissues were from Harlan Sprague-Dawley rats. Circumvallate and foliate taste papillae were dissected from tongue, and rapidly frozen on dry ice. Poly(A)mRNA was extracted from tissues by direct binding to oligo dT-cellulose (FastTrack II kit, Invitrogen, Carlsbad, Calif.). Unless stated otherwise, taste tissue samples were from juvenile (pre-weaning 16 to 20 day-old) rats.

5' and 3'-RACE and RT-PCR

Initial 5' RACE (rapid amplification of cDNA ends) reactions were carried out using superscript reverse transcriptase followed by terminal deoxynucleotidyl transferase (both from Gibco-BRL, Gaithersburg, Md.)[44]. Subsequently, the Marathon RACE system (Clontech Laboratories, Palo Alto, Calif.) was employed for generating and cloning RACE products. Poly(A)RNA, extracted from vallate and foliate papilla, was used to synthesize double strand cDNA, which was then ligated to an adapter-primer. Nested gene-specific primers were designed in the core region of rat mGluR4 cDNA sequence within the 800-bp region known to be expressed in taste buds[17]. RACE reactions in both directions were carried out using Klentaq DNA polymerase (Clontech) or Elongase (BRL) to ensure amplification of long products. Annealing steps were at the highest temperature permitted by respective primers. Amplification proceeded for 25–30 cycles to minimize nonspecific products. Amplification products were electrophoresed and blot hybridized to identify mGluR4-related bands, which were then cloned into pGEM-T vector (Promega) and sequenced on an ABI Sequencer Model 373A.

The following primers based on mGluR4a cDNA[33] (with identifying amino acid positions) were used in reverse transcriptase-polymerase chain reaction (RT-PCR):

B: 5' (D266) CGACAAGATCATCAAACTGCCTAC 3' (SEQ ID NO.:3)

R: 5' (F455) GAAGTTGACGTTCCTGATGTACT 3' (SEQ ID NO.:4)

To isolate a genomic fragment that contained 'intron a', genomic DNA was amplified with primers located in cDNA sequence: forward primer B (above) and a reverse primer at F307-N301. The following primers were based on intron sequence derived from genomic clones, and were used to map whether the entire intron a was represented in precursor nuclear RNAs (FIG. 2a):

RNase Protection Assay

Figure 2B:
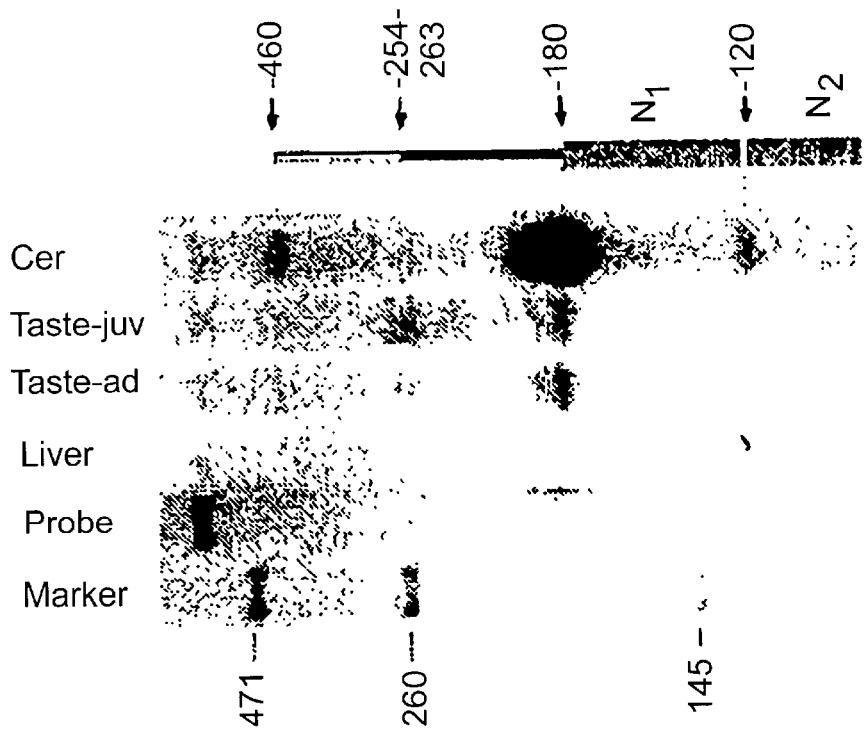
FIG. 2b shows an RNase protection assay demonstrating that taste tissue contains significant amounts of truncated mGluR4 RNA, wherein lengths are indicated in nucleotides, RNA markers are on the left, RNase-protected fragments are on the right, and a schematic of the probe used shows exons (gray) and the segment of intron a found in taste-derived mGluR4 cDNA (black)

The template for mGluR4 probe was constructed by ligating together a genomic fragment and a cDNA fragment at a shared AflII site located 32 bp upstream of the junction between intron a and exon $N_1$ (FIGS. 1b and 2b). The genomic fragment contained the downstream 400 bp of intron a (extended for 368 bp upstream of the AflII site). The 210 bp cDNA segment of the chimeric probe began at the AflII site in intron a and included two sequential exons, $N_1$, and part of $N_2$. The resulting construct in pGEM-T vector was used to transcribe an antisense probe (FIG. 2b) with at least 238 nt complementary to taste-mGluR4 mRNA, as predicted from the sequence of the longest 5' RACE done (see Results). [$^{32}$P]-labeled antisense RNA was transcribed using T7 RNA polymerase. Hybridization and RNase digestion were performed using the High-Speed Hybridization RPA kit from Ambion (Austin, Tex.). Protected fragments were analyzed on denaturing 6% polyacrylamide-urea gels.

Transfection

Full-length cDNAs for brain-mGluR4 and taste-mGluR4 were reconstructed from cerebellar or taste poly(A)RNA respectively, by RT-PCR using Elongase (BRL) for high-fidelity amplification. The brain-mGluR4 insert included 7 nucleotides of 5' untranslated region; the taste-mGluR4 insert included 100 nucleotides of presumed 5' UTR upstream of the first in-frame start codon. Both cDNA inserts terminated at their common stop codon (following I912), yielding the mGluR4a version of the C terminus[33]. The inserts were cloned into the EcoRI site of pcDNA3.1 vector (Invitrogen).

CHO cells were transfected with brain-mGluR4 and taste-mGluR4 constructs and with non-recombinant pcDNA3.1 vector, all in parallel, using a cationic lipid, DMRIE-C (Gibco-BRL). Cells with stably integrated plasmid were selected and maintained in 300 µg per ml G418 starting 24 h after transfection. The medium consisted of Dulbecco's Modified Eagle Medium (D-MEM) supplemented with 10% fetal bovine serum, 2 mM glutamine, 1.7 mM proline and 100 units per ml penicillin-streptomycin[35]. Clones were lifted within two weeks and screened for expression by western blot analysis. A single clone for each form was propagated for functional assays. Stably transfected but non-clonal lines of cells from independent transfections with both forms of mGluR4 and non-recombinant vector were also maintained and used in functional assays.

Immunoblot Analysis

Anti-peptide anti-serum directed against the C-terminal 18-amino acid sequence of mGluR4a was raised in rabbits and antibody was purified by affinity chromatography (Zymed Laboratories, San Francisco, Calif.). This epitope is shared between both brain-mGluR4 and taste-mGluR4 described herein. Lysates of transfected CHO cells were electrophoresed and tested for expression of brain-mGluR4 and taste-mGluR4 by immunoblot analysis[45] on PVDF membrane. Detection was with alkaline phosphatase-conjugated secondary antibody and CSPD chemiluminescent substrate (both from Tropix, Bedford, Mass.). Bands on autoradiographs were densitometrically quantified as needed.

T1: 5' (48 by upstream of R292) CAGCTGGGTAGCCTTACATGTCT 3' (SEQ ID NO.:5)

T2: 5' (400 by upstream of R292) TCTGGAGTAGGATCAGGTGGATG 3' (SEQ ID NO.:6).

T3: 5' (2000 by upstream of R292) AAAGGCTGCTATCTCGTGGACT 3' (SEQ ID NO.:7).

Functional Assay

CHO cells, stably transfected with brain-mGluR4, taste-mGluR4 or non-recombinant pcDNA3.1, were maintained as sub-confluent cultures and refed every two days to minimize chronic stimulation of expressed receptors by glutamate released from dead cells. Cells were plated 20 h before assay in a 96-well microtiter plate at 2×10[4] cells per 200 μl well. Fresh medium was replaced for one hour immediately before assaying receptor function as described[35]. Briefly, cells were incubated in Dulbecco's phosphate buffered saline containing 1 mM IBMX for 20 min followed by stimulation for 10 min in 10 μM forskolin and 1 mM IBMX, with or without agonists. Stimulation buffer was rapidly removed, and cells were lysed in 200 μl 0.25% dodecyltrimethyl-ammonium bromide in 50 mM acetate buffer (Amersham, Piscataway, N.J.). Released cAMP in 20% of each lysate was assayed directly using an Amersham EIA-based kit and plotted as mean±s.e. of 3–6 experiments, each performed with triplicate wells of cells.

Example 1

In-situ hybridization shows that mGluR4 is expressed in rat taste buds and cannot be detected in surrounding non-sensory epithelium[17,21]. However, it is unclear from these data whether mGluR4 in taste buds is identical to that in the brain. Earlier RT-PCR and in-situ hybridization analyses focused on an ~800-bp core region conserved among mGluR1–8 (represented by the double line in FIG. 1b). The N terminus of mGluRs comprises a large extracellular glutamate-binding domain[29]. The cytoplasmic C terminus of mGluRs participates in interactions with G proteins. Because N and C termini of mGluRs determine essential functional characteristics, the corresponding sequences for mGluR4 expressed in taste tissue were analyzed.

Full-length cDNA for mGLuR4 from Taste Tissue

In the brain, mGluR4 mRNA is found in two forms, mGluR4a and mGluR4b, which differ at the 3' end[32]. The longer mRNA includes an exon containing an in-frame stop codon, and thus generates a shorter protein product, mGluR4a. To analyze the C terminus of mGluR4 in taste cells, poly(A)RNA from taste (circumvallate and foliate) papillae and gene-specific primers located in the previously characterized 800-bp core region were used. 3' RACE (rapid amplification of cDNA ends) reactions were performed and the longest specifically amplified bands were cloned. DNA-sequence analysis of representative clones yielded 100% identity with mGluR4a cDNA from the brain[33]. RT-PCR with a primer pair straddling the alternatively spliced exon was also undertaken. The principal amplification product was confirmed by DNA sequence analysis to be mGluRa. A faint band corresponding in size to mGluR4b was detected only in occasional PCRs. Thus, it was concluded that the C-terminal sequence in taste tissue was predominantly of the mGluR4a type.

Gene-specific reverse primers in the 800 bp core region were also used in 5' RACE reactions. Previously cloned cDNAs for rat mGluR4a include a 5' untranslated region (5' UTR) of either 69 bp[33] or 854 bp[29]. Thus, it was estimated that the 5' RACE products should range between 1450 and 2235 bp. Using brain poly(A)RNA to validate the method, amplification products extending to ≧2000 bp were obtained as expected. In contrast, the 5' RACE product obtained in parallel from taste tissue terminated abruptly at approximately 600 bp. Similarly truncated products from taste-derived mRNA resulted from 5' RACE reactions with at least four different gene-specific reverse primers and two sources of reverse transcriptase.

A Distinct mGluR4 cDNA Found in Taste Tissue

Sequence analysis of the cloned RACE product indicated that the 5' terminal 40–60 bp of the taste-derived cDNA clones were novel, showing no similarity to any region of brain mGluR4 cDNA (FIG. 1a). A stop codon, shown in FIG. 1a as a triangle, was found near the 5' end, in-frame with the long open reading frame, implying that the 5' end is untranslated sequence. Two potential start codons were found in frame, 102 bp and 189 bp downstream of the stop codon. Thus, the sequence of mGluR4 cDNA from taste tissue is unique for the first ~60 bp and then is identical for at least 2220 bp to mGluR4a cDNA from brain. Sequence identity begins abruptly at the codon for R291.

The point of divergence between unique and identical sequences for taste- and brain-derived cDNAs, located at amino acid R291 of mGluR4a, resembles a splice acceptor site. To test this hypothesis, a genomic fragment was amplified from this region and it was determined that an intron (shown as intron a in FIG. 1b, the location of which is depicted by a black inverted triangle in FIG. 1a) interrupts the codon for R291. The 3' end of intron a is identical to the approximately 60 bp unique sequence at the 5' end of the taste-derived mGluR4 cDNAs (FIGS. 1a and b). One additional intron was also identified further downstream.

Example 2

Taste-tissue mGluR4 is a Mature mRNA

Figure 2A:
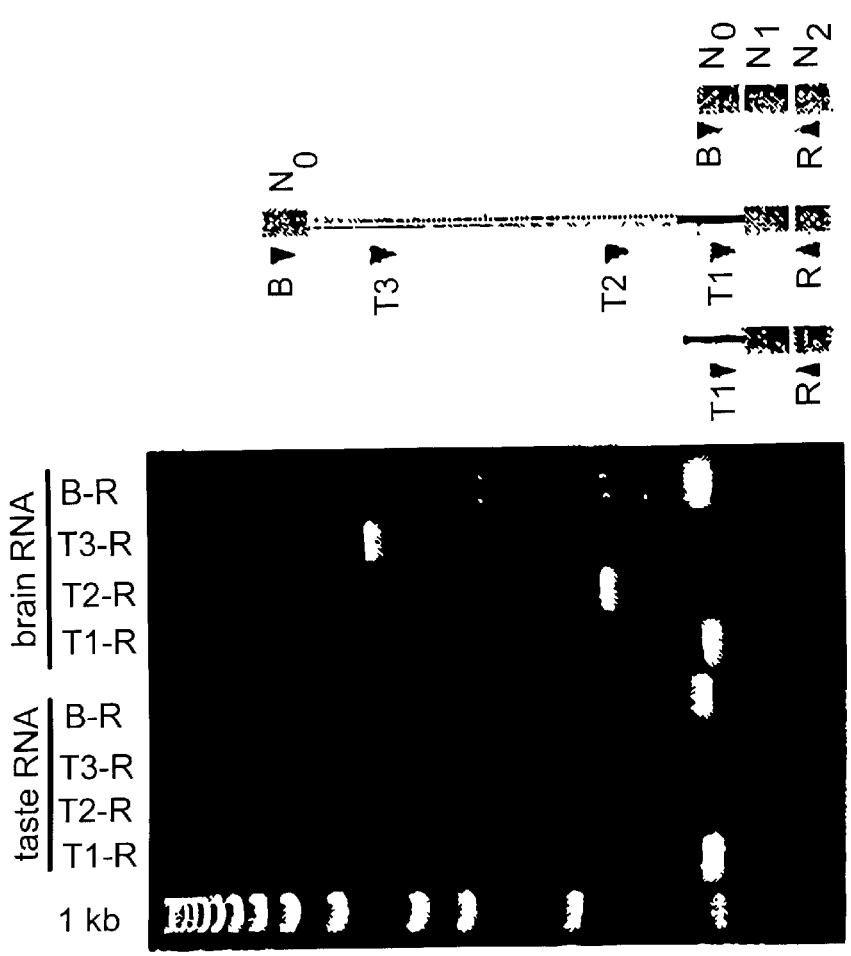
FIG. 2a shows a gel in which RT-PCR products obtained using poly(a) RNA from taste tissue (visible in lanes amplified with T1-R and b-R primer pairs) and from brain (visible in lanes amplified with all three primer pairs T1, T2 and T3) have been separated, and schematics on the right show RNA templates postulated to yield the PCR products obtained (taste-mGluR4, precursor of brain-mGluR4 and mature brain-mGlur4, respectively)

The presence of intron sequence in the taste-derived mGluR4 cDNA raised the possibility that it was amplified from a nuclear (precursor) RNA rather than a mature mRNA. Because introns are spliced out intact, a precursor RNA should include the complete sequence of intron a. This prediction was tested by RT-PCR (FIG. 2a). Three forward primers (T1, T2 and T3) along intron a were used. The reverse primer (R) was selected from a separate downstream exon to preclude amplification from genomic DNA. From brain poly(A)RNA, approximately equal amounts of product were detected for all three reactions using forward primers within intron a (FIG. 2a). This result implies that intron a may be a late-spliced intron and that brain poly(A)RNA contains pre-cursor RNAs that include the complete intron. In contrast, taste poly(A)RNA showed amplification product only from the farthest-downstream intronic primer, T1, and not from upstream primers T2 or T3. Thus, poly(A)RNA in taste tissue included only a short segment from the 3' end of intron a, suggesting that the truncated mGluR4 cDNAs obtained in 5' RACE were probably derived not from an unspliced precursor RNA, but from a mature mRNA. A forward primer (B) located in the next exon upstream ($N_0$), amplified from the previously known mGluR4 mature mRNA, served as a control. PCR product from mGluR4 mRNA lacking this intron was detected in poly(A)RNA from both brain and taste papillae. Precursor RNAs are typically found in tissue at considerably lower concentration than their respective mature mRNAs. In taste tissue, the low concentration of mature full-length mGluR4 mRNA[17] precludes detecting its precursor RNA (as RT-PCR products with T3 and T2 primers).

RNA secondary structure can cause premature termination of reverse transcripts and yield truncated products in 5' RACE. This did not seem to be the case for the truncated taste-mGluR4 cDNA because brain poly(A)RNA did yield long 5' RACE products, and because precursor RNAs in brain samples were readily reverse transcribed and amplified through intron a (FIG. 2a). Thus, based on the 5' RACE and RT-PCR analyses above, it was tentatively concluded that taste tissue may contain two forms of mGluR4 mRNA, i.e. one similar to the known mGluR4a[33] and another with a truncated 5' end.

Because RT-PCR can detect RNAs that are present in minor (nonphysiological) quantities in cells, tests were conducted to determine whether the truncated mGluR4 RNA found in taste tissue was present at significant concentration using RNase protection (FIG. 2b), an independent method not based on amplification. The probe for this assay consisted of the last ~400 nucleotides of intron a, followed by 178 nucleotides in two consecutive exons, $N_1$ and (part of) $N_2$. No bands were generated with RNA from liver, a control tissue that does not express mGluR4, demonstrating the specificity and RNase sensitivity of the probe. The known full-length form of mGluR4 mRNA (henceforth designated 'brain-mGluR4') should protect a band of 178 nucleotides, as it includes no sequence from intron a. Indeed, consistent with an identity as brain-mGluR4, a protected band of ~80 nucleotides was detected in poly(A)RNA from cerebellum and, at a lower concentration, from taste papillae. In addition, we detected two bands corresponding to precursor nuclear RNA when cerebellar poly(A)RNA was used in RNase protection. Because exons $N_1$ and $N_2$ are not contiguous in the genome, precursor RNA protected fragments ~460 nucleotides long (400 nucleotides of intron a plus exon $N_1$) and ~120 nucleotides (fragment of exon $N_2$). The absence of these precursor bands in taste samples indicated that genomic DNA (which would protect the same size bands as precursor RNA) was not a significant contaminant in the taste samples.

In addition to bands derived from the known mGluR4 mRNA and its precursor RNA, hybridization with poly(A) RNA from taste papillae yielded an additional band. This was a broad band, 254–263 nucleotides in length, as might be expected for an RNA that included the 178 nucleotides of exon ($N_1$ plus $N_2$) sequence and extended 76–85 nucleotides forward into intron a. This protected band was consistent with the mGluR4 cDNA cloned in the 5' RACE experiments. The band was not detected in cerebellar RNA lanes. Thus, this form of mGluR4 RNA, which includes a part of intron a, was designated as 'taste-mGluR4'. Of note is that the ~178-bp band derived from brain-mGluR4 is sharp, as expected, whereas the broad taste-mGluR4-derived band indicates more heterogeneity in length. The 5' ends of mRNAs frequently show such heterogeneity, spanning 3–15 nucleotides.

The broad band corresponding to taste-mGluR4 mRNA was observed in three separate protection experiments using different batches of poly(A)RNA from taste tissue of juvenile rats. Densitometric analysis from three experiments indicated that taste-mGluR4 mRNA is present at 70–120% of the concentration of brain-mGluR4 mRNA in taste tissue from juvenile rats. Interestingly, the taste-mGluR4 band was found at lower concentration when poly(A)RNA from adult rather than juvenile rats was used for protection (FIG. 2b).

Example 3

Taste-mGluR4 is a Functional mRNA

Figure 3A:
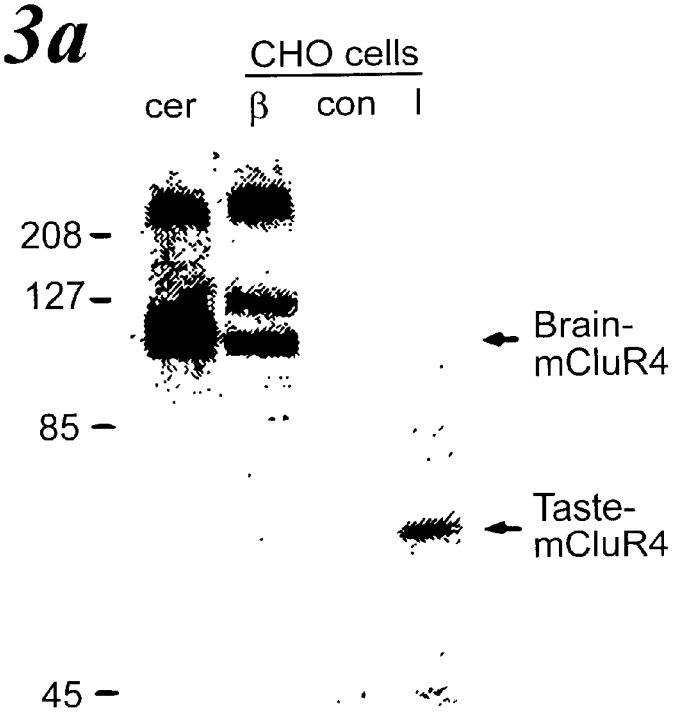
FIG. 3a depicts an immunoblot of CHO cells stably transfected with brain-mGluR4 (B) or taste-mGluR4 (T) showing a prominent immunoreactive band of predicted molecular weight (about 102 kDa and about 68 kDa, respectively) when probed with an antibody against the shared C terminus of both forms.

To determine whether taste-mGluR4 is a functional mRNA, full-length clones for both forms of mGluR4 in pcDNA3.1 vector were generated, transfected into CHO cells and selected stable transfectants. When probed with an antibody against the C terminus of mGluR4a, immunoblots (FIG. 3a) of cerebellar extracts contained a strong band of the expected molecular weight, ~102 kDa, as previously reported[30]. A presumed dimer at ~210 kDa was also detected. Clones of cells stably transfected with brain-mGluR4 showed prominent bands of the same size as in cerebellum (FIG. 3a). In contrast, CHO cells transfected with the taste-mGluR4 construct consistently showed a prominent band of ~68 kDa, corresponding to the size predicted from the cDNA sequence. Neither the ~102-kDa nor ~68-kDa bands was present in parallel lanes containing lysates of CHO cells transfected with non-recombinant pcDNA vector. Thus, the truncated taste-mGluR4 mRNA characterized from taste tissue was indeed a functional mRNA that was translated into immunologically recognizable protein.

Sequencing analysis using the forward primer defined by SEQ ID. NO: 12 (5'atttgaattcAGCTGGGTAGCCTTAC ATGTC 3') and reverse primer SEQ ID NO.:11 (5'taaagaattCTAGATGGCATGGTTGGTGTAG 3') revealed the mRNA sequence of SEQ ID NO.:1, as shown in Table 1. Lower case letters in the primer sequences denote additional bases added to generate restriction site for cloning.

TABLE 1

| Taste-Specific mGLUR4 mRNA Sequence | | | | |
|---|---|---|---|---|
| GCCTGGGGCA | CCGGCACACA | GACTAGGGCA | GCTGGGTAGC | CTTACATGTC TGGGCTGGGT |
| TGCTGTGTCC | CCACAGGAGG | GTGTTGGAGG | CAGCTCGCAG | GGCCAACCAG ACCGGCCACT |
| TCTTTTGGAT | GGGTTCTGAT | AGCTGGGGCT | CCAAGAGTGC | CCCTGTGCTG CGCCTTGAGG |
| AGGTGGCCGA | GGGCGCAGTC | ACCATTCTCC | CCAAGAGGAT | GTCTGTTCGA GGGTTCGACC |
| GATACTTCTC | CAGCCGCACG | CTGGACAACA | ACAGGCGCAA | CATCTGGTTT GCCGAGTTCT |
| GGGAGGACAA | CTTCCATTGC | AAGTTGAGCC | GCCACGCGCT | CAAGAAGGGA AGCCACATCA |
| AGAAGTGCAC | CAACCGAGAG | CGCATCGGGC | AGGACTCGGC | CTATGAGCAG GAGGGGAAGG |
| TGCAGTTCGT | GATTGACGCT | GTGTACGCCA | TGGGCCACGC | GCTGCACGCC ATGCACCGTG |
| ACCTGTGTCC | TGGCCGCGTA | GGACTCTGCC | CTCGCATGGA | CCCCGTGGAT GGCACCCAGC |
| TGCTTAAGTA | CATCAGGAAC | GTCAACTTCT | CAGGCATTGC | GGGGAACCCT GTAACCTTCA |
| ATGAGAACGG | AGACGCACCA | GGGCGCTACG | ACATCTACCA | GTACCAACTG CGCAATGGCT |
| CGGCCGAGTA | CAAGGTCATC | GGCTCGTGGA | CAGACCACCT | GCACCTCAGA ATAGAGCGGA |
| TGCAGTGGCC | AGGGAGTGGC | CAGCAGCTGC | CGCGCTCCAT | CTGCAGTCTG CCCTGCCAGC |

TABLE 1-continued

Taste-Specific mGLUR4 mRNA Sequence

```
CCGGGGAGCG AAAGAAGACT GTGAAGGGCA TGGCTTGCTG CTGGCACTGC GAGCCCTGCA
CCGGGTACCA GTACCAAGTG GACCGCTACA CCTGTAAGAC CTGCCCCTAC GACATGCGGC
CCACAGAGAA CCGCACGAGC TGCCAGCCCA TCCCCATCGT CAAGTTGGAG TGGGACTCGC
CGTGGGCCGT GCTGCCCCTC TTCCTGGCCG TGGTGGGCAT CGCCGCCACG CTGTTCGTGG
TGGTCACGTT TGTGCGCTAC AACGATACCC CCATCGTCAA GGCCTCGGGC CGGGAGCTGA
GCTACGTGCT GCTGGCGGGC ATCTTTCTGT GCTACGCCAC TACCTTCCTC ATGATCGCAG
AGCCGGACCT GGGGACCTGT TCGCTCCGCC GCATCTTCCT AGGGCTCGGC ATGAGCATCA
GCTACGCGGC CCTGCTGACC AAGACCAACC GCATTTACCG CATCTTTGAG CAGGGCAAAC
GGTCGGTCAG TGCCCCGCGT TTCATCAGCC CGGCCTCGCA GCTGGCCATC ACCTTCATCC
TCATCTCCCT GCAGCTGCTC GGCATCTGCG TGTGGTTCGT GGTGGACCCC TCCCACTCGG
TGGTGGACTT CCAGGACCAA CGGACACTTG ACCCCCGCTT TGCCAGGGGC GTGCTCAAGT
GCGACATCTC GGACCTGTCC CTCATCTGCC TGCTGGGCTA CAGCATGCTG CTGATGGTCA
CGTGTACTGT GTACGCCATC AAGACCCGAG GCGTGCCCGA GACCTTCAAC GAGGCCAAGC
CCATCGGCTT CACCATGTAC ACCACCTGCA TTGTCTGGCT GGCCTTCATC CCCATCTTTT
TTGGCACCTC ACAGTCAGCC GACAAGCTGT ACATCCAGAC AACCACACTG ACTGTCTCCG
TGAGTCTGAG CGCTTCAGTG TCCCTGGGGA TGCTCTACAT GCCCAAAGTC TACATCATGC
TCTTCCACCC GGAGCAGAAC GTGCCCAAGC GCAAGCGCAG TCTCAAAGCC GTGGTCACCG
CCGCCACCAT GTCCAACAAG TTCACACAGA AGGGCAACTT CAGGCCCAAT GGGGAAGCCA
AATCAGAGCT GTGTGAGAAC CTGGAGACCC CAGCGCTGGC TACCAAACAG ACCTACGTCA
CCTACACCAA CCATGCCATC TAGCCGGGCC GCGGAGCCAA GCAGGCTAAG GAGCCACAAC
CTCTGAGGAT GGCACATTGG CCAGGGCCG TTCCCGAGGG CCCTGCCGAT GTCTGCCCGC
CTCCCGGGCA TCCACGAATG TGGCTTGGTG CTGAGGACAG TAGAGACCCC GGCCATCACT
GCTGGGCAAG CCGTGGTGGG CAACCAGAGG AGGCCGAGTG GCTGGGGCAG TTCCAGGTTA
TGCCACACAC AGGTCTTCCT TCTGGACCAC TGTTGGGCCC AGCCCCAAAG CACAGGGGCT
CGGTCTCCAG AGCCCAGCCC TGGCTTCCTC TCCTTCCTCC TGCCTCCGTC TGTCCTGTGG
GTGACCCCGG TTGGTCCCTG CCCCGTCTTT ACGTTTCTCT TCCGTCTTTG CTCTGCATGT
GTTGTCTGTT TGGGCCCTCT GCTTCCATAT TTTTCCATTC TGCTCCTGGC CTTCCCCTGC
CATCTGCCCT GCCCCCTGCC CCTCCTCCCT GAGCTGCCCC ATCCCCCGCA TCATTTTCTC
TTCTGTTCCC CCTCGATCTC ATTTCCTACC AGCCTTCCCC CTACTTGGCT TCATCCACCA
ACTCTTTCAC CACGTTGCAA AAGAGAAAAA AAAGGGGGG GGGGAATCAC CCCCTACAAA
AAAGCCCAAA CAAAAACTAA TCTTGAGTGT GTTTCGAAGT GCTGCGTCCT CCTGGTGGCC
TGTGTGTCCC TGTGGCCTGC AGCCTGCTCG CCCGCCCTAC CCGTCTGCCG TGTGTCCTGC
CCGCCCGCCT GCCCGCCTTG CCCTTCCTGC TAACGACACG GAGTTCAGTG CCTGGGTGTT
TGGTGATGGT CTCTGATGTG TAGCATGTCT GTTTTTATAC CGAGAACATT TCTAATAAAG
ATAAACACAT GGTTTTGC
```

The corresponding amino acid sequence, defined by SEQ ID NO.: 13 is set forth in Table 2.

TABLE 2

Taste-Specific mGLUR4 Amino Acid Sequence

MGSDSWGSKS APVLRLEEVA EGAVTILPKR MSVRGFDRYF SSRTLDNNRR NIWFAEFWED

NFHCKLSRHA LKKGSHIKKC TNRERIGQDS AYEQEGKVQF VIDAVYAMGH ALHAMHRDLC

PGRVGLCPRM DPVDGTQLLK YIRNVNFSGI AGNPVTFNEN GDAPGRYDIY QYQLRNGSAE

YKVIGSWTDH LHLRIERMQW PGSGQQLPRS ICSLPCQPGE RKKTVKGMAC CWHCEPCTGY

QYQVDRYTCK TCPYDMRPTE NRTSCQPIPI VKLEWDSPWA VLPLFLAVVG IAATLFVVVT

FVRYNDTPIV KASGRELSYV LLAGIFLCYA TTFLMIAEPD LGTCSLRRIF LGLGMSISYA

ALLTKTNRIY RIFEQGKRSV SAPRFISPAS QLAITFILIS LQLLGICVWF VVDPSHSVVD

FQDQRTLDPR FARGVLKCDI SDLSLICLLG YSMLLMVTCT VYAIKTRGVP ETFNEAKPIG

FTMYTTCIVW LAFIPIFFGT SQSADKLYIQ TTTLTVSVSL SASVSLGMLY MPKVYIILFH

PEQNVPKRKR SLKAVVTAAT MSNKFTQKGN FRPNGEAKSE LCENLETPAL ATKQTYVTYT

NHAI*

Example 4
Taste-mGluR4 is Negatively Coupled to cAMP

Figure 3B:
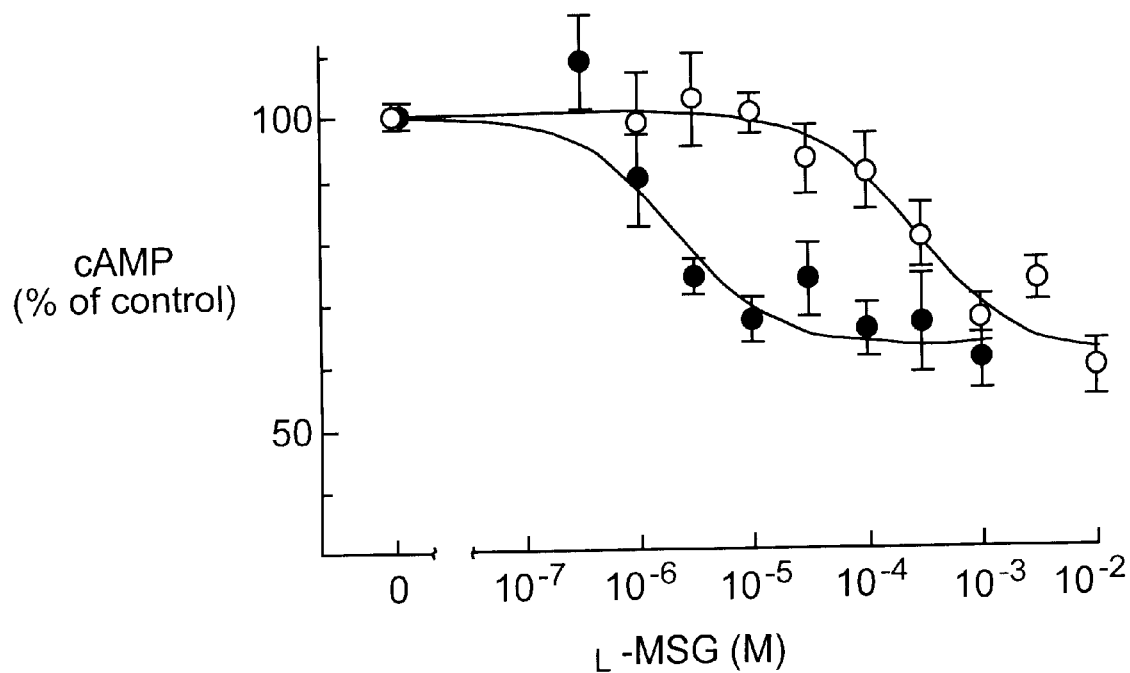
FIG. 3b graphically depicts changes in cAMP levels in CHO cells expressing brain-mGluR4 and taste-mGluR4 receptors in response to glutamate stimulation in the presence of forskolin and IBMX.

In transfected CHO cells, activation of group III mGluRs leads to a suppression of forskolin-stimulated cAMP synthesis[35]. CHO cells stably expressing brain-mGluR4 responded predictably to L-glutamate, as evidenced in six triplicate experiments, each including triplicate wells of cells exposed to each concentration of l-glutamate tested (FIG. 3b). The $EC_{50}$ for this response was 2 μM glutamate, consistent with earlier reports on mGluR4a (5 μM)[35]. Cells expressing taste-mGluR4 displayed no response to L-glutamate at concentrations of 30 μM or below. The $EC_{50}$ for L-glutamate for taste-mGluR4 was calculated to be 280 μM glutamate. The possibility that a low cell-surface density of taste-mGluR4 was considered as an explanation of the low efficacy (high $EC_{50}$) noted. Thus, two separate lines of CHO cells expressing taste-mGluR4 were examined. Expression levels of taste-mGluR4 (as determined by immunoblot) were 100-fold and 2-fold lower, respectively, than in parallel lines expressing brain-mGluR4. Nevertheless, the $EC_{50}$ values for the two lines expressing taste-mGluR4 were very similar, 300 and 250 μM, respectively. The consistently high $EC_{50}$ for taste-mGluR4 suggests that low receptor density does not explain its low efficacy. Instead, the data suggest that taste-mGluR4 is approximately two orders of magnitude less sensitive to L-glutamate than is brain-mGluR4. Direct measurements of affinity are expected to confirm this interpretation.

Because the concentration of L-glutamate required for taste-mGluR4 was high, consideration was given to the possibility that osmotic or other nonspecific effects might influence the cAMP response. Thus, mGluR4-expressing cells were stimulated with D-glutamate, an isomer that does not elicit umami taste[36]. Relative to controls, cells stimulated with 1 MM D-glutamate yielded cAMP levels of 126±17% (brain-mGluR4) or 99±3% (taste-mGluR4). Control CHO cells transfected with non-recombinant vector did not alter cAMP concentrations upon treatment with either L-glutamate (1 mM, 127±16%; 10 mM, 132±19%; n=9) or D-glutamate. Thus, receptor-independent mechanisms do not seem to decrease cAMP.

Example 5
Taste-mGluR4 Responds to L-AP4

Figure 4:
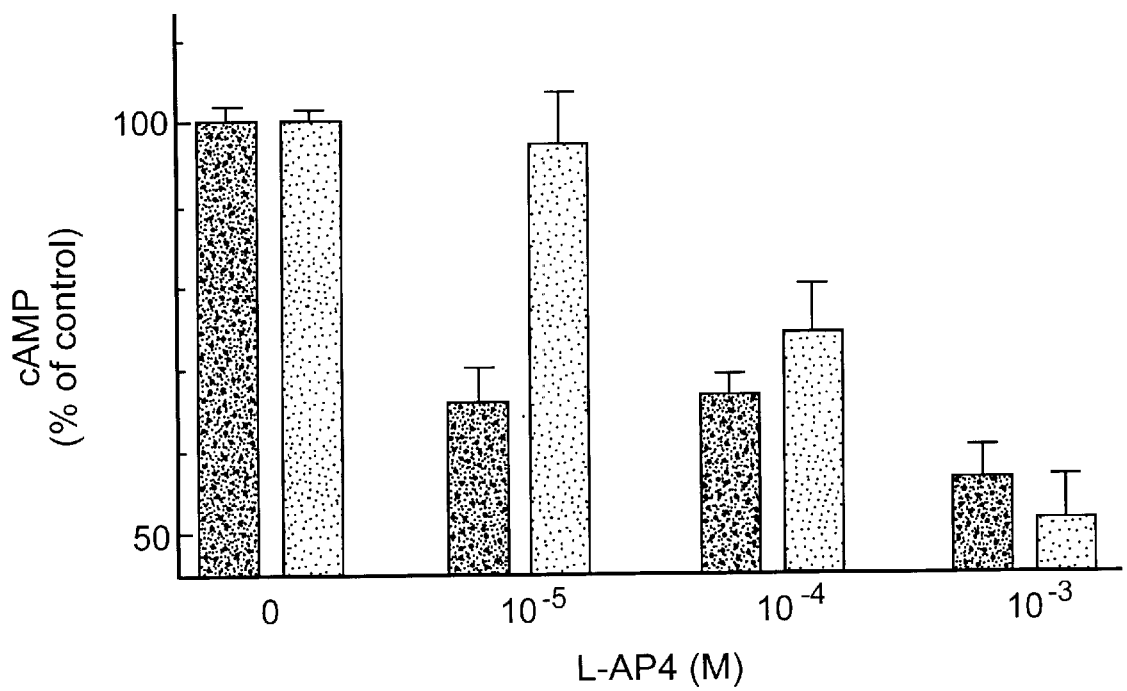
FIG. 4 graphically depicts activation of brain-mGluR4 and taste-mGluR4 by the MSG mimic L-AP4.

In rat and human behavioral studies, L-AP4 mimics the taste of L-MSG[17,22]. Accordingly, a taste receptor for L-MSG would be expected to be stimulated by L-AP4 as well. To ascertain whether the identified putative taste-mGluR4 protein meets the L-MSG "mimic" criterion, measurements were made of taste-mGluR4 responses to L-AP4 in a concentration range effective for eliciting taste sensations in mammals. CHO cells expressing brain-mGluR4 responded to L-AP4 by suppressing forskolin-stimulated cAMP production. The response seemed to saturate these receptors at all concentrations of L-AP4 above 10 μM (FIG. 4), as expected from the published $EC_{50}$ of 0.5–1.0 μM[35]. By contrast, cells expressing taste-mGluR4 showed no response to 10 μM L-AP4, whereas 100 μM and 1 mM L-AP4 gave progressively larger responses. Behavioral assays have shown that 100 μM L-AP4 is near the MSG taste detection threshold in rats[17]. Thus, taste-mGluR4 responds to L-AP4 over a concentration range similar to that observed for L-AP4 taste. The cAMP levels in control cells transfected with non-recombinant vector did not change upon treatment with L-AP4.

In summary, mGluR4 is a metabotropic glutamate receptor originally characterized from the brain. In situ hybridization analyses have shown that this receptor is also expressed in taste buds[17,21]. The present data demonstrate that mGluR4 in taste tissue is expressed as a structurally and functionally distinct form that of the brain, a receptor termed 'taste-mGluR4'. Taste-mGluR4 is a truncated version of the previously characterized brain receptor, and lacks ~50% of the receptor's extracellular N terminus. This truncation is particularly significant, because the N terminus of metabotropic glutamate receptors is believed to contain the glutamate-binding domain[29], and changes in this region are likely to influence the affinity of the receptor for ligands. Indeed, the truncated taste-mGluR4 was found to be much less sensitive to L-glutamate and L-AP4 than the full-length brain form, implying a reduced affinity for these agonists. Importantly, the reduced sensitivity of taste-mGluR4 corresponds well with the concentrations of L-glutamate and L-AP4 needed to elicit a response in gustatory receptor cells in situ. The data are fully consistent with the interpretation that the novel taste-mGluR4 is a taste receptor for umami, the taste quality elicited by L-MSG.

The molecular identification and characterization of taste receptors has lagged behind research on other sensory receptors, notably, receptors for vision and olfaction. GPCRs are present in taste tissue[13,14]; receptors with sequences related to those of the mGluRs[15]. Although mRNA and/or protein for such candidate taste receptors has been demonstrated in lingual tissue, the lack of functional expression has hampered ligand identification and validation of their physiological significance. One of the challenges in studying the function of taste receptors is the high concentrations of stimuli needed. In the case of sugars, salts, and glutamate, the detection thresholds of gustatory sensory cells in nerve recordings or behavioral tests are in the range of a few hundred micromolar and higher. The low sensitivity of taste receptors, which may result from low affinity for ligands, has complicated binding assays and functional tests. By utilizing a high concentration of glutamate and a selective glutamate receptor ligand (L-AP4), characterization of the function of taste-mGluR4 in transfected cells has been achieved.

The taste-mGluR4 cDNA exemplified herein was cloned from posterior (circumvallate and foliate) taste papillae of juvenile rats. The threshold concentration for activating taste-mGluR4 (30 $\mu$M) matches well with the threshold (100 $\mu$M) reported for glutamate taste responses in the glossopharyngeal nerve of juvenile mice[26]. Interestingly, taste nerve thresholds in adult mice and rats, at 2–10 mM, are significantly higher[26,27]. The studies discussed herein show that the mRNA for taste-mGluR4 is expressed at lower concentration in adult than in juvenile rats[17] (FIG. 2b), which may explain the decreased sensitivity to MSG taste noted in adult rodents.

L-AP4 is a highly effective ligand for brain-mGluR4 receptors[35]. L-AP4 mimics the taste of glutamate in rats[17] and is an umami stimulus in humans[22]. The Examples discussed herein show that L-AP4 also stimulates taste-mGluR4, at concentrations effective as taste stimuli. MAP4, an antagonist of brain-mGluR4, fails to block taste nerve responses to glutamate and L-AP4 in chorda tympani nerve recordings[23]. Tests of MAP4 on cloned taste-mGluR4 may help to resolve this seeming paradox.

A distinctive feature of umami is the potentiation of glutamate responses by the nucleotide monophosphates of inosine and guanosine (IMP and GMP). This synergy is well documented in human psychophysical studies[37], animal behavioral experiments[24], gustatory nerve recordings[27] and patch-clamp studies[25]. Synergistic interactions are also found between L-AP4 and nudeotides[23,24], further underscoring the importance of taste-mGluR4 to umami transduction. The site of interaction between glutamate and nucleotides remains to be defined, but might involve synaptic convergence of separate gustatory sensory cells onto common afferent fibers, or converging signaling pathways from separate receptors within the same glutamate-sensing taste bud cell. It is also possible that both glutamate and nucleotides interact with a common receptor molecule. For instance, ligand-binding studies on bovine taste membranes suggested an allosteric model for nucleotide effects on glutamate taste[38]. The cloned taste-mGluR4 will allow direct tests of such models of receptor-taste stimulus interactions.

RT-PCR and RNase protection analyses indicate that both taste-mGluR4 and brain-mGluR4 are expressed in taste tissue (FIGS. 2a and 2b). Glutamate is implicated as a neurotransmitter for taste bud afferent synapses[39], and brain-mGluR4 could serve as an autoreceptor at such synapses. These data suggest that taste-mGluR4 is likely to function as an umami receptor, whereas brain-mGluR4 may serve as a neurotransmitter receptor at synapses in or near taste papillae.

Glutamate receptors other than mGluR4 may be expressed in gustatory sensory cells. For example, patch-damp recordings, $Co^{2+}$ uptake, and $Ca^{2+}$ imaging on rat and mouse taste buds suggest that glutamate activates both ionotropic and metabotropic glutamate receptors[18,25,39,40]. However, all these experiments exposed both apical and basolateral membranes of taste receptor cells to glutamate. Given that bona-fide taste stimulation reaches only the apical membrane of taste receptor cells, it is critical to note that behavioral studies and nerve recordings (which stimulate only the apical membrane) indicate a minimal role for ionotropic-like glutamate receptors in taste transduction for L-MSG[17,22-24]. Thus, baso-lateral synapses on gustatory receptor cells may include glutamate receptors other than taste-mGluR4.

Transcripts of several mGluRs, including mGluR1 and mGluR5, are alternatively spliced[41,42]. For mGluR4, alternative splicing gives rise to receptors with either long or short C termini[32]. In spite of considerable structural diversity, most alternative-splicing variants of mGluRs show only subtle changes in their functional properties. For instance, mGluR1c and mGluR1a elicit distinct temporal patterns of $Ca^{2+}$ release[42]. The characteristics of taste-mGluR4 demonstrate that substantially different functions exist for two receptors derived from the same gene. Presently, the molecular mechanism by which the truncated mRNA is produced in taste cells is unclear. Possibly, an alternative splice acceptor site is located within intron a and the 5' RACE reactions disclosed herein did not progress into additional exons upstream of the ~60 bp in intron a. Nevertheless, the presence of an in-frame stop codon within these ~60 nucleotides implies that any additional exons would constitute 5' UTR of the mRNA and would not affect the sequence of the translated protein. An alternative possibility is that the origin for transcription of taste-mGluR4 mRNA is located within intron a. Multiple promoters yielding mRNAs with distinct 5' exons occur in the mGluR5 gene[43], meaning a similar transcription strategy is plausible in the mGluR4 gene.

The subject matter of the preferred embodiments is discussed by Chaudhari et al. in a an a published article (Chaudhari, N, et al., *Nature Neuroscience*, 3(2):113–119 (February 2000), the entire disclosure of which is hereby incorporated herein by reference.

References

1. Lindemann, B. Taste reception. *Physiol. Rev.* 76, 719–766 (1996).
2. Lindemann, B. Receptor seeks ligand: on the way to cloning the molecular receptors for sweet and bitter taste. *Nat. Med.* 5, 381–382 (1999).
3. McLaughlin, S. K., McKinnon, P J. & Margolskee, R. F Gustducin is a taste-cell-specific G protein closely related to the transducins. *Nature* 357, 563–569 (1992).
4: McLaughlin, S. K., McKinnon, P J., Spickofsky, N., Danho, W & Margolskee, R. F. Molecular cloning of G proteins and phosphodiesterases from rat taste cells. *Physiol. Behav.* 56, 1157–1164 (1994).
5. Kusakabe, Y, Abe, K., Tanemura, K., Emori, Y. & Arai, S. GUST27 and closely related G-protein-coupled receptors are localized in taste buds together with $G_i$-protein α-subunit. *Chem. Senses* 21, 335–340 (1996).
6. Kusakabe, Y et al. Identification of two alpha-subunit species of GTP-binding proteins, Gα15 and Gαq, expressed in rat taste buds. *Biochim. Biophys. Acta* 1403, 265–272 (1998).
7. Huang, L. et al. Gγ13 colocalizes with gustducin in taste receptor cells and mediates $IP_3$ responses to bitter denatonium. *Nat. Neurosci.* 2,1055–1062 (1999).
8. Misaka, T. et al. Taste buds have a cyclic nucleotide-activated channel, CNGgust. *J. Biol. Chem.* 272, 22623–22629 (1997).
9. Kretz, O., Barbry P., Bock, R. & Lindemann, B. Differential expression of RNA and protein of the three pore-forming subunits of the amiloride-sensitive epithelial sodium channel in taste buds of the rat. *J. Histochem. Cytochem.* 47, 51–64 (1999).
10. Lin, W., Finger, T. E., Rossier, B. C. & Kinnamon, S. C. Epithelial Na+ channel subunits in rat taste cells: localization and regulation by aldosterone. J. Comp. Neurol. 405, 406–420 (1999).
11. Ogawa, S. et al. Receptor that leaves a sour taste in the mouth. Nature 395, 555–556 (1998).
12. Ming, D., Ruiz-Avila, L. & Margolskee, R. E Characterization and solubfization of bitter-responsive receptors that couple to gustducin. Proc. Nad. Acad. Sci. USA 95, 8933–8938 (1998).
13. Matsuoka, I., Mori, T., Aoki, J., Sato, T. & Kurihara, K. Identification of novel members of G-protein coupled receptor superfamily expressed in bovine taste tissue. *Biochem. Biophys. Res. Commun.* 194, 504–511 (1993).
14. Abe, K., Kusakabe, Y, Tanemura, K., Emori, Y & Arai, S. Primary structure and cell-type specific expression of a gustatory G protein-coupled receptor related to olfactory receptors. *J. Biol. Chem.* 268, 12033–12039 (1993).
15. Hoon, M. A. et al. Putative mammalian taste receptors: a class of taste-specific GPCRs with distinct topographic selectivity. Cell 96, 541–551 (1999).
16. Faurion, A. Are umami taste receptor sites structurally related to glutamate CNS receptor sites? Physiol. Behav. 49, 905–912 (1991).
17. Chaudhari, N. et al. The taste of monosodium glutamate: Membrane receptors in taste buds. ). Neurosci. 16, 3817–3826 (1996).
18. Hayashi, Y, Zviman, M. M., Brand, J. G., Teeter, J. H. & Restrepo, D. Measurement of membrane potential and [Ca2+]i in cell ensembles: Application to the study of glutamate taste in mice. Biophys. J. 71, 1057–1070 (1996).
19. Conn, P J. & Pin, J. P Pharmacology and functions of metabotropic glutamate receptors. Annu. Rev. Pharmacol. Toxicol. 37, 205–237 (1997).
20. Chaudhari, N. & Roper, S. D. Molecular and physiological evidence for glutamate (umami) taste transduction via a G protein-coupled receptor. Ann. NY Acad. Sci. 855, 398–406 (1998).
21. Yang, H., Wanner, I. B., Roper, S. D. & Chaudhari, N. An optimized method for in situ hybridization with signal amplification that allows the detection of rare mRNAs. J. Histochem. Cytochem. 47 431–446 (1999).
22. Kurihara, K. & Kashiwayanagi, M. Introductory remarks on umami taste. Ann. NY Acad. Sci. 855, 393–397 (1998).
23. Sako, N. & Yamamoto, T Analyses of taste nerve responses with special reference to possible receptor mechanisms of umami taste in the rat. Neurosci. Lett. 261, 109–112 (1999).
24. Delay, E. R et al. Taste preference synergism between glutamate receptor ligands and IMP in rats. Chem. Senses (in press).
25. Lin, W & Kinnamon, S. C. Physiological evidence for ionotropic and metabotropic glutamate receptors in rat taste cells. J. Neurophysiol. 82, 2061–2069(1999).
26. Ninomiya, Y, Tanikukai, T., Yoshida, S., Funakoshi, M. & Tanimukai, T. Gustatory neural responses in preweanling mice. PhysioL Behav. 49, 913–918 (1991).
27. Yamamoto, T et al. Electrophysiological and behavioural studies on the taste of umami substances in the rat. Physiol. Behav. 49, 919–925 (1991).
28. Monastyrskala, K. et al. Effect of the umami peptides on the ligand binding and function of rat mGlu4a receptor might implicate this receptor in the monosodium glutamate taste transduction. Br. J. Pharmacol. 128, 1027–1034 (1999).
29. O'Hara, E J. et al. The ligand-binding domain in metabotropic glutamate receptors is related to bacterial periplasmic binding proteins. Neuron 11, 41–52 (1993).
30. Han, G. & Hampson, D. R Ligand binding to the amino-terminal domain of the mGluR4 subtype of metabotropic glutamate receptor. J. Biol. Chem. 274, 10008–10013(1999).
31. Takahashi, K., Tsuchida, K., Tanabe, Y., Masu, M. & Nakanishi, S. Role of the large extracellular domain of metabotropic glutamate receptors in agonist selectivity determination.]. Biol. Chem. 268, 19341–19345 (1993).
32. Thomsen, C. et al. Cloning and characterization of a metabotropic glutamate receptor, mGluR4b. Neuropharmacology 36, 21–30 (1997).
33. Tanabe, Y, Masu, M., Ishii, T., Shigemoto, R & Nakanishi, S. A family of metabotropic glutamate receptors. Neuron 8, 169–179 (1992).
34. Bradley, S. R, Levey, A. I., Hersch, S. M. & Conn, P J. Immunocytochemical localization of group III metabotropic glutamate receptors in the hippocampus with subtype-specific antibodies. J. Neurosci. 16, 2044–2056 (1996).
35. Tanabe, Y et al. Signal transduction, pharmacological properties and expression patterns of two rat metabotropic glutamate receptors, mGluR3 and mGluR4. J. Neurosci. 13, 1372–1378 (1993).
36. Hettinger, T P, Frank, M. E. & Myers, W E. Are the tastes of polycose and monosodium glutamate unique? Chem. Senses 21, 341–347 (1996).
37. Rifkin, B. & Bartoshuk, L. M. Taste synergism between monosodium glutamate and disodium 5'-guanylate. PhysioL Behav. 24, 1169–1172 (1980).
38. Torii, K. & Cagan, R. H. Biochemical studies of taste sensation. DC. Enhancement of L-[3H]glutamate binding to bovine taste papillae by 5'-ribonudeotides. Biochim. Biophys. Acta 627, 313–323 (1980).
39. Calcedo, A., Kim, K. & Roper, S. Glutamate-induced cobalt uptake reveals non-NMDA receptors in rat taste cells. J. Comp. Neurol. (in press).
40. Bigiani, A., Delay, R J., Chaudhari, N., Kinnamon, S. C. & Roper, S. D. Responses to glutamate in rat taste cells. J. NeurophysioL 77, 3048–3059 (1997).
41. Pin, J. P & Duvoisin, R. The metabotropic glutamate receptors: structure and functions. Neuropharmacology 34, 1–26 (1995).
42. Pin, J.-P, Waeber, C., Prezeau, L., Bockaert, J. & Heinemann, S. E Alternative splicing generates metabotropic glutamate receptors inducing different patterns of calcium release in *Xenopus oocytes*. Proc. NatL Acad Sci. USA 89, 10331–10335(1992).
43. Yamaguchi, S. & Nakanishi, S. Regional expression and regulation of alternative forms of mRNAs derived from two distinct transcription initiation sites of the rat mGluR5 gene. *J. Neurochem.* 71, 60–68 (1998).
44. Frohman, M. A., Dush, M. K. & Martin, G. R Rapid production of full-length cDNAs from rare transcripts:

amplification using a single gene-specific oligonucleotide primer. *Proc. Natl. Acad. Sci. USA* 85, 8998–9002 (1988).
45. Towbin, H., Staehelin, T. & Bordon, J. Electrophoretic transfer of proteins from polyacrylamide gels to nitrocellulose sheets: Procedure and some applications. *Proc Nat. Acad Sci. USA* 76, 4350–4354 (1979).
46. Zhou, X. and Chaudhari, N. *Chem. Senses* 22, 834 (1997).

While the invention has been described in connection with what is presently considered to be the most practical and preferred embodiments, it should be understood that the invention is not limited to the disclosed embodiment. To the contrary, the invention disclosed herein is intended to encompass various modifications and equivalent arrangements included within the spirit and scope of the appended claims. Variations in, for example, structural aspects of receptor not affecting ligand binding, the MSG mimics used and MSG expression vectors can be made without departing form the novel aspects of this invention as defined in the claims.

What is claimed is:

1. A rat metabotropic glutamate taste receptor having a molecular weight of approximately 68 kDa, comprising the amino acid sequence of SEQ ID NO:13.

2. The glutamate taste receptor of claim 1, wherein the receptor functions as a umami taste receptor.

3. The glutamate taste receptor of claim 1, wherein the receptor responds to monosodium L-glutamate binding by decreasing cellular levels of cAMP.

4. The glutamate taste receptor of claim 1, wherein the receptor exhibits a truncated extracellular N-terminal domain when compared with neurotransmitter mGluR4 metabotropic glutamate receptors, and comprises about 50% fewer amino acids than are present in neurotransmitter mGluR4 metabotropic glutamate receptors.

5. The glutamate taste receptor of claim 4, wherein the extracellular N-terminal domain is followed by seven transmembrane helices and an intracellular cytoplasmic C-terminus.

* * * * *